(12) United States Patent
Yazaki et al.

(10) Patent No.: US 6,211,375 B1
(45) Date of Patent: *Apr. 3, 2001

(54) PYRIDONECARBOXYLIC ACID DERIVATIVES OR SALTS THEREOF AND ANTIBACTERIAL AGENTS CONTAINING THE SAME AS THE ACTIVE INGREDIENT

(75) Inventors: Akira Yazaki; Yoshiko Niino; Yoshihiro Ohshita; Norihiro Hayashi; Hirotaka Amano; Yuzo Hirao; Tamae Yamane, all of Hiroshima (JP)

(73) Assignee: Wakunaga Pharmaceutical Co., Ltd., Hiroshima (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/171,411
(22) PCT Filed: Apr. 17, 1997
(86) PCT No.: PCT/JP97/01327
    § 371 Date: Jan. 20, 1999
    § 102(e) Date: Jan. 20, 1999
(87) PCT Pub. No.: WO97/40036
    PCT Pub. Date: Oct. 30, 1997

(30) Foreign Application Priority Data

Apr. 19, 1996 (JP) .................................................. 8-122538

(51) Int. Cl.⁷ ............................................... C07D 215/56
(52) U.S. Cl. .............................................................. 546/156
(58) Field of Search ............................................. 546/156

(56) References Cited

U.S. PATENT DOCUMENTS

| 4,146,719 | 3/1979 | Irikura . | |
|---|---|---|---|
| 5,910,498 | * 6/1999 | Yazaki et al. | ................ 514/255 |

FOREIGN PATENT DOCUMENTS

| 5531042 | 3/1980 | (JP) . |
| 5746986 | 3/1982 | (JP) . |
| 60228479 | 11/1985 | (JP) . |
| 62-135458 | 6/1987 | (JP) . |
| 63-79885 | 4/1988 | (JP) . |
| 4-74167 | 3/1992 | (JP) . |
| 5-262738 | 10/1993 | (JP) . |
| 6-25224 | 2/1994 | (JP) . |
| 9612704 | 5/1996 | (WO) . |
| 9623775 | 8/1996 | (WO) . |

OTHER PUBLICATIONS

Abstract of JP 58074667 May 1983.

* cited by examiner

Primary Examiner—Patricia L. Morris
(74) Attorney, Agent, or Firm—Birch, Stewart, Kolasch & Birch, LLP

(57) ABSTRACT

A novel pyridonecarboxylic acid derivative or its salt exhibiting satisfactory antibacterial activities, intestinal absorption, metabolic stability, and reduced side effects, in particular, phototoxicity and cytotoxicity, as well as an antibacterial agent containing such pyridonecarboxylic acid derivative or its salt are provided.

For such an object, a pyridonecarboxylic acid derivative represented by the following formula (1):

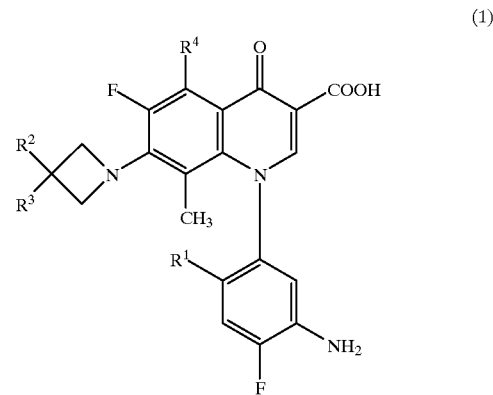

(1)

(wherein $R^1$ represents hydrogen atom, a halogen atom or a lower alkyl group; $R^2$ represents hydrogen atom or a lower alkyl group; $R^3$ represents substituted or unsubstituted amino group or hydroxyl group; and $R^4$ represents hydrogen atom, a lower alkyl group, amino group or nitro group) or its salt is provided.

5 Claims, No Drawings

PYRIDONECARBOXYLIC ACID DERIVATIVES OR SALTS THEREOF AND ANTIBACTERIAL AGENTS CONTAINING THE SAME AS THE ACTIVE INGREDIENT

This application is the national phase under 35 U.S.C. §371 of prior PCT International Application No. PCT/JP97/01327 which has an International filing date of Apr. 17, 1997 which designated the United States of America, the entire contents of which are hereby incorporated by reference.

TECHNICAL FIELD

The present invention relates to novel pyridonecarboxylic acid derivatives or their salts having excellent antibacterial activities and oral absorption, and antibacterial agents containing the same.

BACKGROUND TECHNOLOGY

Many compounds having a basic skeleton of pyridonecarboxylic acid are known to be useful synthetic antibacterials for their excellent antibacterial activities and wide antibacterial spectrum. Among such compounds, norfloxacin (Japanese Patent Application Laid-open No. 53-141286), enoxacin (Japanese Patent Application Laid-Open No. 55-31042), ofloxacin (Japanese Patent Application Laid-Open No. 57-46986), ciprofloxacin (Japanese Patent Application Laid-Open No. 58-74667), tosufloxacin (Japanese Patent Application Laid-Open No. 60-228479), and the like are widely used in clinical practice for treating infections.

These compounds, however, need further improvements in antibacterial activities, intestinal absorption, metabolic stability, and side effects, and in particular, in phototoxicity and cytotoxicity.

SUMMARY OF THE INVENTION

The present invention has been completed in view of such situation, and an object of the present invention is to provide novel pyridonecarboxylic acid derivatives or the salts thereof having satisfactory antibacterial activities, intestinal absorption and metabolic stability, and reduced side effects, in particular, phototoxicity and cytotoxicity; and antibacterial agents containing the same.

In order to achieve the above object, the inventors of the present invention have made an intensive study to find compounds which would be excellent synthetic antibacterial agents in clinical practice, and found that novel compounds represented by the following general formula (1) have good antibacterial activities to gram negative and positive bacteria as well as an extremely low toxicity, and therefore, would be very useful synthetic antibacterial agents. The present invention has been accomplished on the bases of such a finding.

According to the present invention, there is provided pyridonecarboxylic acid derivatives or their salts represented by the following formula (1):

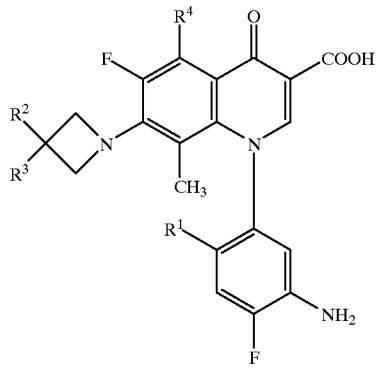

[In the formula, $R^1$ represents hydrogen atom, a halogen atom or a lower alkyl group; $R^2$ represents hydrogen atom or a lower alkyl group; $R^3$ represents substituted or unsubstituted amino group or hydroxyl group; and $R^4$ represents hydrogen atom, a lower alkyl group, amino group or nitro group.]

According to the present invention, there is also provided antibacterial agents containing the pyridonecarboxylic acid derivatives or their salts as their effective components.

BEST MODE FOR CARRYING OUT THE INVENTION

The novel pyridonecarboxylic acid derivatives of the present invention are represented by the general formula (1) as shown above, and the term "lower" used for the substituents of the pyridonecarboxylic acid derivatives represented by the general formula (1) designates that the substituent comprises 1 to 7 carbon atoms, and preferably 1 to 5 carbon atoms in the case of a linear substituent, and that the substituent comprises 3 to 7 carbon atoms in the case of a cyclic substituent.

The halogen atoms represented by $R^1$ of the general formula (1) include fluorine, chlorine, bromine and iodine atoms, among which fluorine and chlorine atoms are preferred, and fluorine atom is most preferred.

The lower alkyl groups represented by $R^1$, $R^2$ and $R^4$ include methyl group, ethyl group, n-propyl group, i-propyl group, n-butyl group, i-butyl group, t-butyl group, pentyl group, hexyl group, and heptyl group, among which methyl group is preferred.

The substituents of the substituted amino group represented by $R^3$ include lower alkyl groups such as methyl group, ethyl group, n-propyl group, i-propyl group, n-butyl group, i-butyl group, t-butyl group, pentyl group, hexyl group, and heptyl group; lower alkenyl groups such as vinyl group, allyl group, 1-propenyl group, butenyl group, pentenyl group, hexenyl group, and heptenyl group; aralkyl groups containing 7 to 11 carbon atoms such as benzyl group and 1-phenylethyl group; aryl groups containing 6 to 14 carbon atoms such as phenyl group and naphthyl group; lower alkanoyl groups such as formyl group, acetyl group, propionyl group, butyryl group and isobutyryl group; lower alkoxycarbonyl groups such as methoxycarbonyl group and ethoxycarbonyl group; aroyl groups containing 7 to 15 carbon atoms such as benzoyl group and naphthoyl group; amino acid residues such as amino acid residues or oligopeptide residues such as glycyl, leucyl, valyl, alanyl, phenylalanyl, alanyl-alanyl, glycyl-valyl, and glycyl-glycyl-valyl, and the amino acid residues or the oligopeptide residues wherein the functional group thereof is protected with an acyl, a lower aralkyl, or other protective groups which is commonly used in peptide chemistry; and cyclic amino group. One or two substituents which may be the same or different may be selected from the substituents as described above. The compound protected with the amino acid residue or the oligopeptide residue is expected to have an improved water solubility.

Preferable groups represented by $R^3$ include amino group, lower alkylamino groups, di-lower alkylamino groups, lower alkanoylamino groups, amino acid-substituted amino groups, oligopeptide-substituted amino groups, and hydroxyl group. More preferable groups of $R^3$ include amino group, methylamino group, ethylamino group, dimethyamino group, formylamino group, glycyl-amino group, leucyl-amino group, valyl-amino group, alanyl-amino group, alanyl-alanyl-amino group, and hydroxyl group among which the amino group being the most preferred.

Preferable combinations of the $R^2$ and $R^3$ are methyl group or hydrogen atom for the $R^2$ and amino group, methylamino group or hydroxyl group for the $R^3$.

Preferable combinations of the $R^1$, $R^2$ and $R^3$ in the general formula (1) is fluorine atom, chlorine atom or methyl group for the $R^1$, hydrogen atom or methyl group for the $R^2$, and amino group, methylamino group or hydroxyl group for the $R^3$, and the most preferable combination is methyl group for the $R^1$, hydrogen atom for the $R^2$ and amino group for the $R^3$.

The pyridonecarboxylic acid derivatives of the formula (1) or the salts thereof as described above may form either an acid adduct salt or a base adduct salt. The term, salt used herein also includes a chelate salt with a boron compound. Exemplary acid adduct salts include (A) salts with a mineral acid such as hydrochloric acid or sulfuric acid; (B) salts with an organic carboxylic acid such as formic acid, citric acid, trichloroacetic acid, trifluoroacetic acid, fumaric acid, or maleic acid; and (C) salts with a sulfonic acid such as methanesulfonic acid, benzenesulfonic acid, p-toluenesulfonic acid, mesitylenesulfonic acid, or naphthalenesulfonic acid; and exemplary base adduct salts include (A') salts with an alkaline metal such as sodium or potassium; (B') salts with an alkaline earth metal such as calcium or magnesium; (C') ammonium salts; (D') salts with a nitrogen-containing organic base such as trimethylamine, triethylamine, tributylamine, pyridine, N,N-dimethylaniline, N-methylpiperidine, N-methylmorpholine, diethylamine, cyclohexylamine, procaine, dibenzylamine, N-benzyl-β-phenethylamine, 1-ephenamine, or N,N'-dibenzylethylenediamine. Exemplary boron compounds include boron halides such as boron fluoride, and lower acyloxyborons such as acetoxyboron.

The pyridonecarboxylic acid derivatives of the formula (1) or the salts thereof may also be in the form of hydrates or solvates in addition to the non-solvated forms. Accordingly, the compounds of the present invention include all of the crystalline forms, the hydrate forms, and the solvate forms.

The pyridonecarboxylic acid derivatives of the formula (1) or the salts thereof as described above may also be present in the form of optically active substances, and such optically active substances are also within the scope of the compounds of the present invention. Still further, the compounds of the formula (1) may be present in the form of (cis or trans) stereoisomers, and such stereoisomers are also within the scope of the compounds of the present invention.

The pyridonecarboxylic acid derivatives of the formula (1) or the salts thereof of the present invention as described above may be produced by any procedure appropriately selected in accordance with such factors as the type of the substituents, and an exemplary procedure is as described below.

The compounds represented by the general formula (1) may be produced, for example, by the procedure 1 or procedure 2 represented by the reaction scheme as described below:

(Procedure 1)

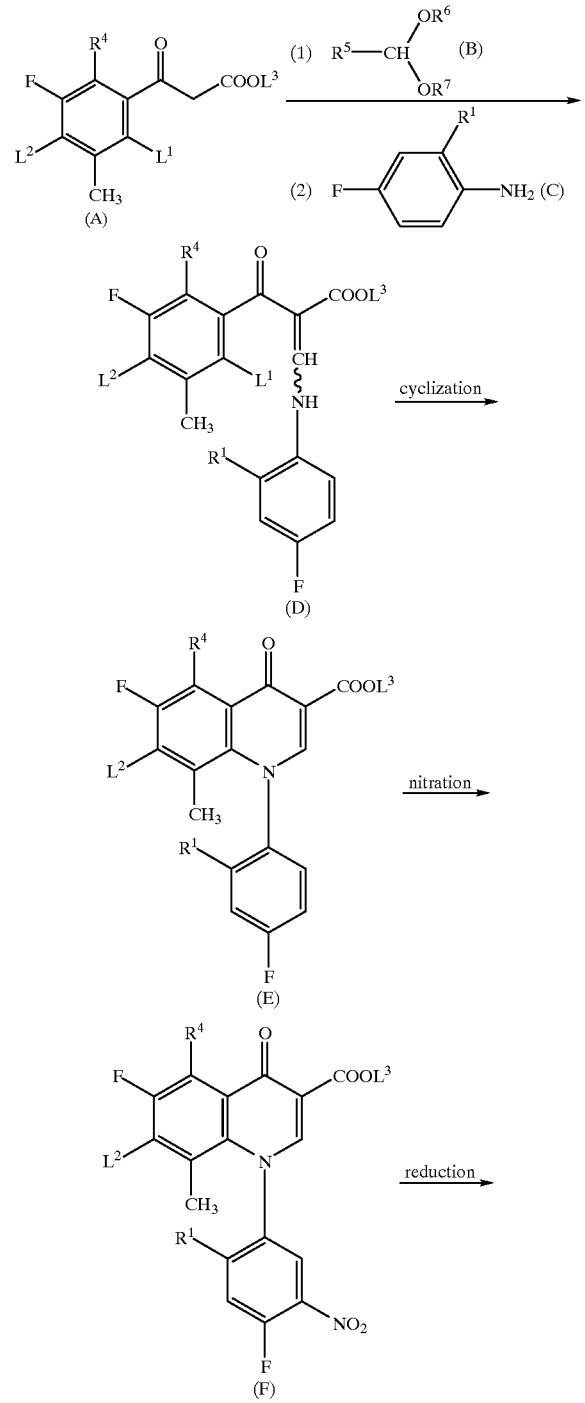

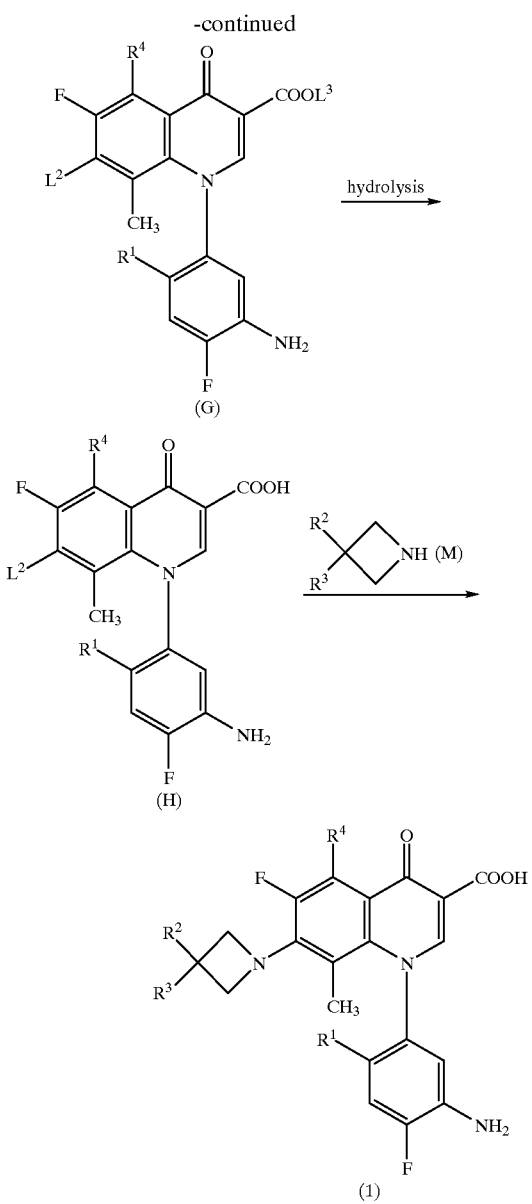

[wherein R⁵ represents a lower alkoxy group or —NR⁸R⁹ group (wherein R⁸ and R⁹ independently represent a lower alkyl group); R⁶ and R⁷ independently represent a lower alkyl group; and L¹ and L² independently represent the same or different halogen atom; L³ represents a lower alkyl group; and R¹, R², R³ and R⁴ are as defined above.]

More illustratively, the compound (1) of the present invention is produced by reacting compound (A) with an orthoformate (B) such as ethyl orthoformate or methyl orthoformate and then, with compound (C) to produce compound (D); cyclizing the compound (D) to produce compound (E); nitrating the compound (E) to produce compound (F); reducing the compound (F) to produce compound (G); hydrolyzing the compound (G) to produce compound (H); and aminating the compound (H) by using an azetidine derivative (M).

The reaction between the compound (A) and the orthoformate (B) is generally carried out at 0 to 160° C., and preferably 50 to 150° C. usually for a reaction period of 10 minutes to 48 hours, and preferably for 1 to 10 hours. In this case, especially not limited, carboxylic anhydride such as acetic anhydride is desirably added in the above reaction. The orthoformate (B) is used in equimolar amount or more to the compound (A), and preferably, in about 1 to 10 times the molar amount to the compound (A).

The reaction with the compound (C) may be effected without any solvent or in a solvent. The solvent used in this reaction may be any solvent as long as the reaction is not affected by the solvent, and the exemplary solvents include aromatic hydrocarbons such as benzene, toluene, and xylene; ethers such as diethylether, tetrahydrofuran, dioxane, monoglyme, and diglyme; aliphatic hydrocarbons such as pentane, hexane, heptane, and ligroin; halogenated hydrocarbons such as methylene chloride, chloroform, and carbon tetrachloride; nonprotonic polar solvents such as dimethylformamide and dimethylsulfoxide; and alcohols such as methanol, ethanol and propanol. This reaction is generally conducted at 0 to 150° C., and preferably at 0 to 100 ° C. usually for a reaction period of 10 minutes to 48 hours. The compound (C) is used in equimolar amount or more to the compound (A), and preferably, in 1 to 2 times the molar amount to the compound (A).

Alternatively, compound (A) may be reacted with an acetal such as N,N-dimethylformamide dimethylacetal or N-dimethylformamide diethylacetal, and then, with compound (C) to produce the compound (D). The solvent used in the reaction with the acetal may be any solvent as long as the reaction is not affected by the solvent, and the exemplary solvents are those described in the foregoing. This reaction is generally conducted at 0 to 150° C., and preferably at room temperature to 100° C. generally for a reaction period of 10 minutes to 48 hours, and preferably for 1 to 10 hours.

Next, the cyclization of the compound (D) into the compound (E) is conducted in an adequate solvent either in the presence or absence of a basic compound. The solvent used in this reaction may be any solvent as long as the reaction is not affected by the solvent, and the exemplary solvents include aromatic hydrocarbons such as benzene, toluene, and xylene; ethers such as diethylether, tetrahydrofuran, dioxane, and monoglyme; halogenated hydrocarbons such as methylene chloride, chloroform, and carbon tetrachloride; alcohols such as methanol, ethanol, propanol, and butanol; and nonprotonic polar solvents such as dimethylformamide and dimethylsulfoxide. Exemplary basic compounds used are alkaline metals such as metal sodium and metal potassium; metal hydrides such as sodium hydride and calcium hydride; inorganic salts such as sodium hydroxide, potassium hydroxide, sodium carbonate, and potassium carbonate; alkoxides such as sodium methoxide, sodium ethoxide, and potassium t-butoxide; metal fluorides such as sodium fluoride and potassium fluoride; organic salts such as triethylamine and 1,8-diazabicyclo[5.4.0]undecene (DBU). This reaction is conducted at a reaction temperature of 0 to 200° C., and preferably, at room temperature to 180° C., and the reaction is generally completed in 5 minutes to 24 hours. The basic compound is used in equimolar amount or more to the compound (B), and preferably, in 1 to 2 times the molar amount to the compound (B).

The nitration of the compound (E) into the compound (F) may be conducted by the procedure generally used in the nitration of aromatic compounds, and mixed acid of nitric acid or nitrate (such as potassium nitrate) in combination with sulfuric acid or acetyl nitrate is used for the nitrating agent. The amount of the mixed acid used in the reaction is such that 1 equivalent or more of sulfuric acid and 1 equivalent or more of nitric acid are used with 1 equivalent of the compound (E), and the reaction is conducted by adding the compound (E) to the mixed acid. The reaction is preferably conducted at a reaction temperature of −10° C. to 80° C. for a period of 5 minutes to 5 hours.

The reduction of the compound (F) into the compound (G) may be conducted by any common procedure such as molten metal reduction wherein zinc, iron, tin, tin chloride (II) or the like is used in an acidic solution; the reduction wherein a sulfate such as sodium sulfate, sodium hydrosulfide, or sodium dithionate is used; and catalytic reduction wherein platinum, Raney nickel, platinum black (Pt—C) or palladium carbon (Pd—C) is used. When formic acid-iron is used, the compound (G) obtained is in the form of a formylamino compound.

The hydrolysis of the compound (G) into the compound (H) may be conducted under any conditions commonly used in the hydrolysis, for example, in the presence of a basic compound such as sodium hydroxide, potassium hydroxide, sodium carbonate, and potassium carbonate, a mineral acid such as hydrochloric acid, sulfuric acid, and hydrobromic acid, or an organic acid such as p-toluenesulfonic acid, and in a solvent such as water, an alcohol such as methanol, ethanol or propanol, or an ether such as tetrahydrofuran or dioxane, a ketone such as acetone or methylethylketone, acetic acid, or a mixture of such solvents. The reaction is generally conducted at room temperature to 180° C., and preferably, at room temperature to 140° C. usually for a reaction period of 1 to 24 hours.

The reaction of the compound (H) with an azetidine derivative (M) for amination of the compound (H) into the compound of formula (1) of the present invention may be conducted in a solvent which does not affect the reaction. Exemplary such solvents include aromatic hydrocarbons such as benzene, toluene, and xylene; alcohols such as methanol and ethanol; ethers such as tetrahydrofuran, dioxane, and monoglyme; halogenated hydrocarbons such as methylene chloride, chloroform, and carbon tetrachloride; and nonprotonic polar solvents such as dimethylformamide, dimethylsulfoxide, N-methylpyrroridone; acetnitrile, pyridine, and the like. The reaction may be conducted in optional presence of neutralizer such as sodium carbonate, calcium carbonate, sodium hydrogencarbonate, triethylamine, and 1,8-diazabicyclo[5.4.0]undecene (DBU), and at a reaction temperature of from room temperature to 160° C., and the reaction is generally completed in several minutes to 48 hours, preferably in 10 minutes to 24 hours. The compound (M) is used in equimolar amount or more to the compound (H), and preferably, in 1 to 5 times the molar amount to the compound (H).

The compound (H) as described above may also be prepared by the following procedure, namely, by the procedure 2.

(Procedure 2)

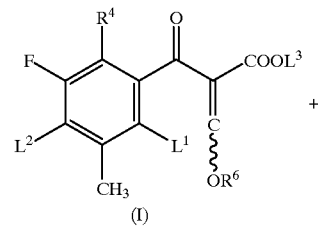

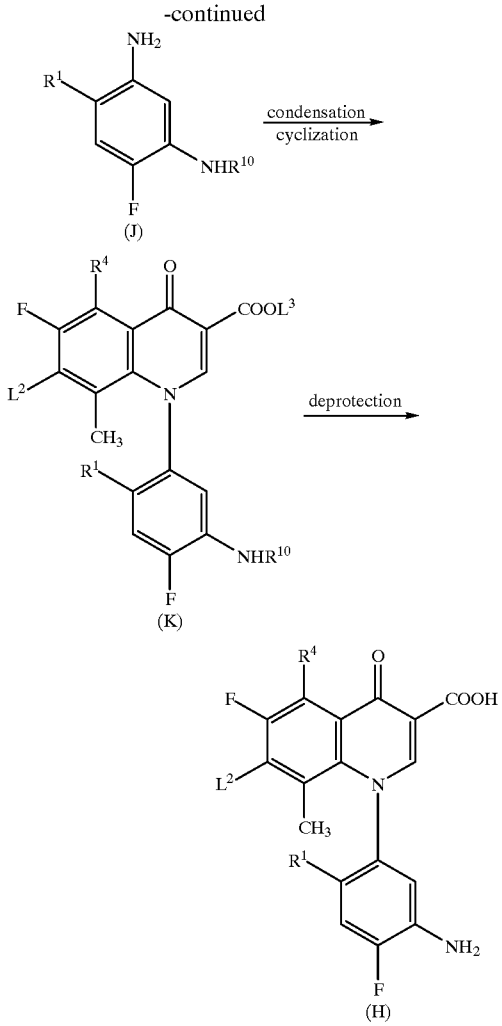

[wherein $R^{10}$ is a protective group for the amino group; and $R^1$, $R^4$, $R^6$, $L^1$, $L^2$ and $L^3$ are as defined above.]

More illustratively, compound (A) is reacted with orthoformate (B) to produce acrylate (I), and the acrylate (I) is reacted with phenylene diamine (J) instead of the compound (C) in the above-described procedure 1 for condensation and cyclization to produce compound (K). The lower alkyl group $L^3$ and the protective group $R^{10}$ for the amino group are then cleaved to obtain compound (H).

The series of steps in the procedure 2 from the compound (I) to the compound (H) may be conducted under the conditions similar to the reactions of the procedure 1 as described above wherein the compound (G) is produced from the compound (A). In the procedure 2, the cleavage of the lower alkyl group $L^3$ and the protective group $R^{10}$ for the amino group (which are typically an acyl group and carbamoyl group, respectively) may be conducted by hydrolysis with an acid or an alkali under the conditions similar to the conditions used in the hydrolysis of the compound (G) into the compound (H) in the procedure 1 as described above.

When amino group, imino group, hydroxyl group, mercapto group, carboxyl group or the like which is not involved in the reaction is present in the starting materials of the procedure 1 or 2 as described above, such group may be protected during the reaction, and the protective group may be eliminated after the completion of the reaction by a conventional method. The protective group used in such a case may be any group as long as the compound of the present invention produced by the reaction can be deprotected with no decomposition in its structure, and any group commonly used in the field of peptide, amino sugar, and nucleic acid chemistry can be used.

2,4,5-trifluoro-3-methylbenzoyl acetate (A') which is a typical starting compounds (A) for the procedures 1 and 2 as described above may be produced by series of steps in the procedure 3 as described below.

(Procedure 3)

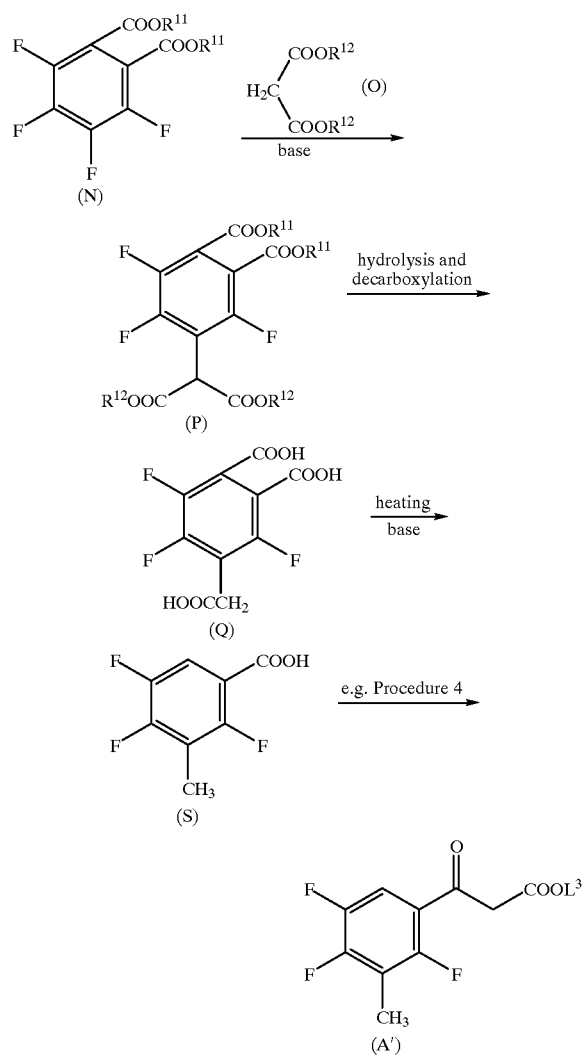

[wherein $R^{11}$ and $R^{12}$ represent lower alkyl groups, and $L^3$ is as defined above.]

Compound (N) is reacted with a malonate (O) in the presence of a basic compound to produce compound (P), and the compound (P) is hydrolyzed and decarboxylated to produce compound (Q). The compound (Q) is heated in the presence of a basic compound to produce compound (S). The thus produced compound (S) is converted into the starting compound (A) by known reactions such as procedure 4 as described below.

The reaction of the compound (N) with the malonate (O) is conducted in the presence of a basic compound and in an appropriate solvent which does not affect the reaction. Exemplary such solvents are aromatic hydrocarbons such as benzene, toluene, and xylene; ethers such as diethylether, tetrahydrofuran, dioxane, monoglyme, and diglyme; aliphatic hydrocarbons such as pentane, hexane, heptane, and ligloin; halogenated hydrocarbons such as methylene chloride, chloroform, and carbon tetrachloride; and nonprotonic polar solvents such as dimethylformamide and dimethylsulfoxide; and alcohols such as methanol, ethanol, and propanol. Exemplary basic compounds used are alkaline metals such as metal sodium and metal potassium; metal hydride such as sodium hydride and calcium hydride; inorganic salts such as sodium hydroxide, potassium hydroxide, sodium carbonate, and potassium carbonate; alkoxides such as sodium methoxide, sodium ethoxide, and potassium t-butoxide; metal fluorides such as sodium fluoride and potassium fluoride; and organic salts such as triethylamine and 1,8-diazabicyclo[5.4.0]undecene (DBU), among which use of metal oxides such as sodium hydride and calcium hydride are preferred.

The reaction conditions are not particularly limited. The reaction, however, is generally conducted under heating for a reaction period of about 30 minutes to 48 hours. The compound (O) is used in an equimolar amount or more to the compound (N), and preferably, in about 1 to 5 times the molar amount to the compound (N).

The hydrolysis and decarboxylation reactions of the compound (P) into the compound (Q) are conducted in the presence of an acid such as sulfuric acid, hydrochloric acid, hydrobromic acid, and acetic acid, typically, by adding such acid to the compound (P) and refluxing for 1 to 4 days.

The reaction from the compound (Q) to the compound (S) is conducted in the presence of a basic compound, and generally, by heating the reaction system to a temperature in the range of from room temperature to 180° C. for 1 to 48 hours, and preferably, to a temperature of from 100 to 140° C. for 1 to 24 hours. The basic compounds used in this reaction may be the same as those described for the reaction of the compound (N) and the malonate (O), and use of triethylamine is most preferred. Exemplary solvents used are N-methylpyrrolidone, dimethylformamide and dimethylsulfoxide, and N-methylpyrrolidone is most preferred.

The compound (S) is converted into the starting compound (A') by a known process such as procedure 4 as described below. In the procedure 4, the compound (S) is reacted with a chlorine compound such as oxalyl dichloride, phosphorus pentachloride, phosphorus trichloride, phosphoryl chloride, thionyl chloride, or sulfuryl chloride to produce acid chloride (T), and the acid chloride (T) is reacted with a malonate (U) in the presence of magnesium and ethanol to produce compound (V), and the compound (V) is converted into the starting compound (A) by refluxing with addition of paratoluene sulfonic acid and water, as known in the art.

(Procedure 4)

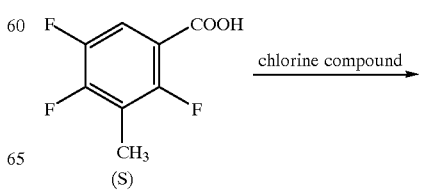

-continued

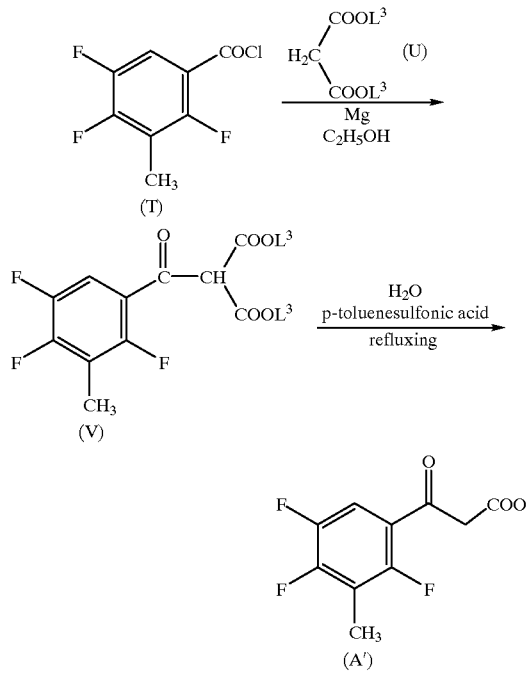

[wherein $L^3$ is as defined above.]

The process of the procedure 3 is most preferred for producing the starting compound (A') since the intermediate (S) can be synthesized by relatively small number of steps at relatively high yield. In addition, the reagents used in the procedure 3 are relatively easy to handle, and the reaction apparatus and treatments are relatively simple. The starting compound (A) may be produced by a process other than the procedure 3, for example, by the process described in the documents as described below or its modification.

1) J. Heterocyclic Chem. 22, 1033 (1985)
2) Liebigs Ann. Chem. 29 (1987)
3) J. Med. Chem. 31, 991 (1988)
4) J. Org. Chem. 35, 930 (1970)
5) Japanese Patent Application Laid-Open No. 62-246541
6) Japanese Patent Application Laid-Open No. 62-26272
7) Japanese Patent Application Laid-Open No. 63-145268
8) J. Med. Chem. 29, 2363 (1986)
9) J. Fluorin Chem. 28, 361 (1985)
10) Japanese Patent Application Laid-Open No. 63-198664
11) Japanese Patent Application Laid-Open No. 63-264461
12) Japanese Patent Application Laid-Open No. 63-104974
13) European Patent Application No. 230948
14) Japanese Patent Application Laid-Open No. 2-282384
15) Published Japanese Translation of PCT International Publication for Patent Application No. 3-502452
16) J. Het. Chem. 27, 1609 (1990)
17) Japanese Patent Application Laid-Open No. 7-215913

For example, the production process described in the document 17) is the process wherein the starting compound (A) is obtained by the procedure 5 as described below.

(Procedure 5)

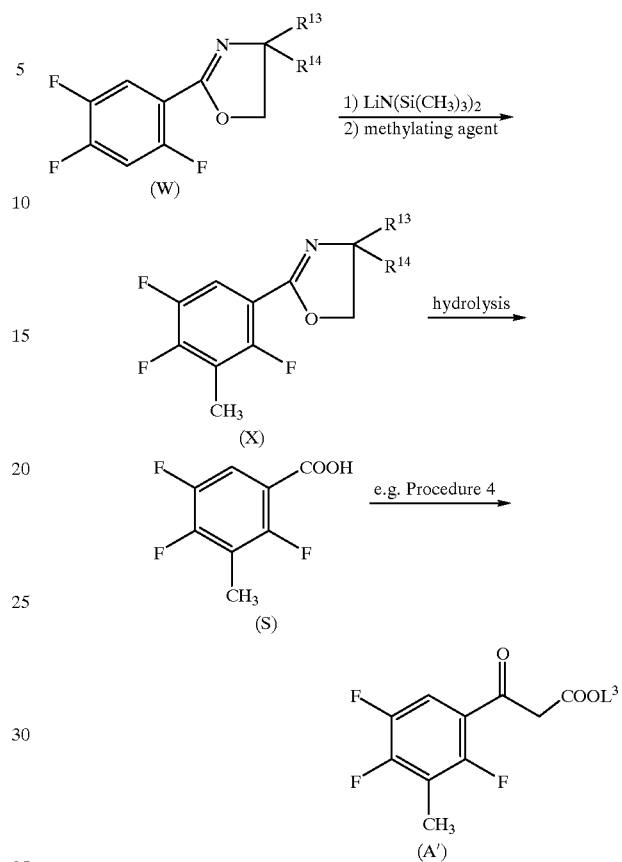

[wherein $R^{13}$ and $R^{14}$ represent lower alkyl groups, and $L^3$ is as defined above.]

In this procedure, compound (W) is first deprotonated with lithium bis(trimethylsilyl)amide and reacted with a methylating agent such as methyl iodide or methyl bromide to produce compound (X), and the compound (X) is hydrolyzed by heating under reflux with an acid such as hydrochloric acid, sulfuric acid or hydrobromic acid to produce compound (S). The compound (S) is then converted into the starting compound (A') as in the above-described process, for example, by procedure 4 as described above.

In this case, lithium bis(trimethylsilyl)amide used as the deprotonating agent in the reaction from the compound (w) to the compound (X) is generally prepared from hexamethyldisilazane and n-butyllithium with no purification. The deprotonation and the methylation reactions are conducted by using an appropriate solvent at a relatively low temperature of from −10° C. to room temperature.

The process of procedure 5 is relatively preferable among the known processes since the synthesis can be accomplished by relatively small number of steps at a relatively high yield. The process of procedure 5, however, is not fully satisfactory in view of industrial scale production since n-butyllithium used in the preparation of lithium bis (trimethylsilyl)amide, the deprotonating agent, is inconvenient to handle since it undergoes spontaneous ignition by contact with oxygen or moisture, and the deprotonation and the methylation reactions have to be conducted at low temperature. Other known processes also suffer from drawbacks such as too many number of steps, complicated reactions, insufficient yield, or the like. The process of procedure 3 is preferable in view of industrial scale production.

The thus obtained compounds of the present invention are isolated and purified in accordance with standard methods. The compounds obtained may be in the form of salts, free carboxylic acids, or free amines depending on the conditions of the isolation and the separation. The forms of the compounds are mutually convertible, and the compounds of the present invention in desired form may be produced.

The compounds (1) or the salts thereof of the present invention have excellent antibacterial activities, intestinal absorption, and metabolic stability, and suffer from reduced phototoxicity, cytotoxicity and other side effects, and therefore, they can be advantageously used as an effective component in antibacterial agents.

The compounds represented by the general formula (1) above or the salts thereof may be formulated into an antibacterial composition with a pharmaceutically acceptable carrier adapted for parenteral administration such as injection, transrectal administration, or eye drop, or oral administration in solid or liquid form.

When the antibacterial composition of the present invention is in the form of an injection, it may be in the form of a solution, a suspension or an emulsion in a pharmaceutically acceptable sterilized water or a non-aqueous medium. Examples of appropriate non-aqueous carriers, diluents, media, and vehicles include propylene glycol, polyethylene glycol, vegetable oils such as olive oil, and organic esters adequate for injection such as ethyl oleate. Such composition may also contain additives such as a preservative, a wetting agent, an emulsifier and a dispersant. The composition may be sterilized, for example, by filtration through a bacteria-removing filter, or by incorporating a sterilizer in the form of a sterilizer or a sterile solid composition soluble in a sterilizable medium for injection just before its use.

A preparation for eye drop administration may preferably contain a solubilizer, a preservative, an isotonizing agent, a thickening agent, and the like in addition to the compounds of the present invention.

Solid preparations for oral administration include capsules, tablets, pills, powders, and granules. In preparing such solid preparations, the compounds of the present invention are typically mixed with at least one inert diluent such as sucrose, lactose or starch. The preparation may also contain substances other than the inert diluents such as lubricant (for example, magnesium stearate etc.). In the case of capsules, tablets or pills, the preparation may also include a buffer. The tablets and the pills may have an enteric coating.

Liquid preparations for oral administration include pharmaceutically acceptable emulsions, solutions, suspensions, syrups and elixirs containing an inert diluent normally used in the art such as water. In addition to such inert diluent, the composition may also contain additives such as a wetting agent, an emulsifying agent, a suspending agent as well as a sweetener, a seasoning, and a flavor. Preparations for enteral administrations may preferably contain an excipient such as cacao butter or suppository wax in addition to the compound of the present invention.

The dose of the compounds (1) of the present invention varies depending on the nature of the compound administered, route of administration, the desired treatment period, and other factors. The compounds of the present invention, however, are typically administered at about 0.1 to 1000 mg/kg per day, and in particular, at about 0.5 to 100 mg/kg per day. If desired, such dose may be administered in 2 to 4 portions.

The compounds (1) and the salts thereof of the present invention exhibit extremely strong antibacterial activities simultaneously with reduced phototoxicity and cytotoxicity, and therefore, would be widely applicable as pharmaceuticals for human and other animals as well as pharmaceuticals for fishes, pesticides, food preservatives, and the like. The compounds of the present invention are also expected to exhibit antivirus properties, and especially, anti-HIV (human immunodeficiency virus) actions, and to be effective in preventing and treating AIDS.

Next, the present invention is described in further detail by referring to Examples, Comparative Examples, and Reference Examples, which by no means limit the scope of the present invention.

REFERENCE EXAMPLE 1

(1) Preparation of diethyl 2-(2,5,6-trifluoro-3,4-bis-(ethoxycarbonyl)phenyl)malonate To 60 ml of tetrahydrofuran was suspended 8 g of sodium hydride from which oil content had been removed by petroleum ether, and 30 ml of tetrahydrofuran solution of 32 g of diethyl malonate was added dropwise to this suspension in an ice bath, and the mixture was stirred at room temperature for 20 minutes. 50 ml of tetrahydrofuran solution of 26.6 g of diethyl 3,4,5,6-tetrafluorophthalate was added dropwise to the reaction solution in an ice bath, and the mixture was stirred at 60° C. for 1 hour. The reaction solution was allowed to cool, and 8 ml of acetic acid was added to the solution and the solution was stirred at room temperature for 20 minutes. To the solution was added chloroform and water to extract the organic layer. The extract was dried over magnesium sulfate and the solvent was distilled off to obtain 50 g of the title compound in crude form.

(2) Preparation of 2-(2,5,6-trifluoro-3,4-dicarboxyphenyl)-acetic Acid

To 50 g of diethyl 2-(2,5,6-trifluoro-3,4-bis(ethoxycarbonyl)phenyl)malonate were added 60 ml of conc. hydrochloric acid and 60 ml of acetic acid, and the mixture was refluxed overnight. The ethyl acetate in the reaction solution was distilled off under reduced pressure, and the solution was refluxed for 2 days. The acid in the reaction solution was distilled off, and hexane was added to the residue. The solid content was collected by filtration and dried to obtain 27 g of the title compound in crude form.
Characteristic features: colorless powder
$^1$HNMR ($d_6$-DMSO) δ; 3.78 (s, 2H).

(3) Preparation of 3-methyl-2,4,5-trifluorobenzoic Acid

To 27 g of 2-(2,5,6-trifluoro-3,4-dicarboxyphenyl)acetic acid was added 28 ml of N-methylpyrrolidone and 10 ml of triethylamine and the mixture was stirred at 140° C. for 2 days. The reaction solution was poured into 6N hydrochloric acid with cooling, and separated by adding diethylether and aqueous solution of sodium hydroxide. The aqueous layer was acidified and extracted with diethylether.

The organic layer was dried over magnesium sulfate and the solvent was distilled off. Hexane was added to the residue., and the solid content was collected by filtration to obtain 12 g of the title compound in powder form.
Characteristic features: colorless needle crystals
Melting point: 97–100° C. $^1$HNMR (CDCl$_3$) δ; 2.29 (d, J=3 Hz, 3H), 7.70 (dd, J=11 Hz, 16 Hz, 1H).

REFERENCE EXAMPLE 2

Preparation of ethyl 2,4,5-trifluoro-3-methylbenzoylacetate 2.4 g of magnesium, 10 ml of ethanol, and 0.4 ml of carbon tetrachloride were stirred in a three necked flask at room temperature for activation, and 15 ml of diethyl malonate and 40 ml of tetrahydrofuran were gradually added dropwise. The mixture was stirred at 80° C. for 4 hours. The reaction solution was allowed to cool, and then cooled to −40° C. To 50 ml solution in methylene chloride of 15.5 g of 2,4,5-trifluoro-3-methylbenzoic acid obtained in Reference Example 1(3) were added 8 ml of oxalyl dichloride and 5 drops of N,N-dimethylformamide, and the mixture was stirred at room temperature for 3 hours. The solvent was distilled off, and tetrahydrofuran was added for azeotropic distillation. The residue was dissolved in 40 ml of tetrahydrofuran, and this solution was gradually added dropwise to the above-described reaction solution at −40° C. After the dropwise addition, the reaction solution was stirred at room temperature for 3 days, and the solvent was distilled off. 50 ml of 12N hydrochloric acid was added to the solution to about pH 2, and the solution was extracted with chloroform, and solvent was distilled off. To the residue were added 30 ml of water and 0.6 g of p-toluenesulfonic acid, and the mixture was stirred under reflux for 6 hours. The reaction solution was allowed to cool, extracted with chloroform, and washed with water and 5% aqueous solution of sodium hydrogencarbonate successively. The organic layer was dried over magnesium sulfate and concentrated under reduced pressure to obtain the title compound as 5.5 g of powder and 10.2 g of brown oil.

REFERENCE EXAMPLE 3

Preparation of ethyl 1-(3-tert-butoxycarbonylamino-4,6-difluorophenyl)-6,7-difluoro-8-methyl-1,4-dihydro-4-oxoguinoline-3-carboxylate To 8.2 g of ethyl 2,4,5-trifluoro-3-methylbenzoylacetate obtained in the Reference Example 2 were added 18.9 g acetic anhydride and 7.0 g of triethyl formate, and the mixture was heated under reflux for 3 hours. The solvent was distilled off, and the residue was azeotropically distilled by adding toluene. To half of the residue was added 10 ml of chloroform, and 3.7 g of N-(tert-butoxycarbonyl)-4,6-difluoro-m-phenylenediamine dissolved in 10 ml of chloroform was added dropwise at 0° C. The mixture was stirred at room temperature for 30 minutes. The solvent was distilled off, and the solid content was collected from the residue by filtration and washed with ethanol to obtain 3.8 g of ethyl 2-(2,4,5-trifluoro-3-methylbenzoyl)-3-(3-tert-butoxycarbonylamino-4,6-difluorophenylamino)acrylate.

To solution of the resulting ethyl 2-(2,4,5-trifluoro-3-methylbenzoyl)-3-(3-tert-butoxycarbonylamino-5 4,6-difluorophenylamino)acrylate in 10 ml of N,N-dimethylformamide was added 1.2 g of potassium carbonate, and the mixture was stirred at 100° C. for 1 hour. The reaction solution was extracted by adding water and ethyl acetate, and organic layer was dried over magnesium sulfate, and the solvent was distilled off. The solid content was collected from the residue by using ethanol and washed with diethylether to obtain 2.9 g of the title compound.
Characteristic features: pale yellow powder
Melting point: 183–185° C. $^1$HNMR (CDCl$_3$) δ; 1.40 (t, J=7 Hz, 3H), 1.51 (s, 9H), 1.82 (d, J=3 Hz, 3H), 4.39 (q, J=7 Hz, 2H), 6.81 (brs, 1H), 7.10 (t, J=10 Hz, 1H), 8.25 (t, J=10 Hz, 1H), 8.29–8.40 (m, 2H).

REFERENCE EXAMPLE 4

Preparation of 1-(3-amino-4,6-difluorophenyl)-6,7-difluoro-8-methyl-1,4-dihydro-4-oxoguinoline-3-carboxylic Acid To 2.8 g of ethyl 1-(3-tert-butoxycarbonylamino-4,6-difluorophenyl)-6,7-difluoro-8-methyl-1,4-dihydro-4-oxoquinoline-3-carboxylate obtained in the Reference Example 3 was added 10 ml of 12N hydrochloric acid, and the mixture was heated under reflux for 4 hours. The reaction solution was allowed to cool, and the solid precipitate was collected by filtration and washed with ethanol and diethylether successively to obtain 1.9 g of the title compound.
Characteristic features: pale yellow powder
Melting point: 266–267° C. $^1$HNMR (d$_6$-DMSO) δ; 1.86 (d, J=3 Hz, 3H), 7.13 (t, J=8 Hz, 1H), 7.46 (t, J=11 Hz, 1H), 8.25 (t, J=9 Hz, 1H), 8.68 (s, 1H)

EXAMPLE 1

7-(3-aminoazetidin-1-yl)-1-(3-amino-4,6-difluorophenyl)-6-fluoro-8-methyl-1,4-dihydro-4-oxoguinoline-3-carboxylic Acid Solution of 70 mg of 3-aminoazetidine·dichloride, 200 mg of 1,8-diazabicyclo[5.4.0]undecene, and 300 mg of pyridine was stirred at 100° C., and to this solution was added 1-(3-amino-4,6-difluorophenyl)-6,7-difluoro-8-methyl-1,4-dihydro-4-oxoquinoline-3-carboxylic acid obtained in the Reference Example 4. The mixture was heated with stirring at 110° C. for 60 minutes. Addition of diethylether to the reaction solution followed by decantation was repeated three times, and 5 ml of ethanol was added with heating to 70° C. The solution was allowed to stand, and the solid precipitate was collected by filtration to obtain 50 mg of the title compound.
Characteristic features: pale yellow powder
Melting point: 213–218° C. $^1$HNMR (d$_6$-DMSO) δ; 1.61 (s, 3H), 3.66–3.81 (m, 2H), 3.82–3.95 (m, 1H), 4.36–4.52 (m, 2H), 5.47 (brs, 2H), 7.04 (t, J=9 Hz, 1H), 7.40 (t, J=10 Hz, 1H), 7.75 (d, J=14 Hz, 1H), 8.48 (s, 1H)

EXAMPLE 2

1-(3-amino-4,6-difluorophenyl)-6-fluoro-8-methyl-7-(3-methylaminoazetidin-1-yl)-1,4-dihydro-4-oxoguinoline-3-carboxylic Acid The procedure of Example 1 was repeated except that 3-aminoazetidine·dichloride was replaced with 110 mg of 3-N-methylaminoazetidine·dichloride to obtain the title compound.
Characteristic features: pale yellow powder
Melting point: 189–194° C. $^1$HNMR (d$_6$-DMSO) δ; 1.64 (s, 3H), 2.20 (s, 3H), 3.78–3.90 (m, 1H), 3.90–4.01 (m, 1H), 4.33–4.50 (m, 2H), 5.50 (brs, 2H), 5 7.02 (t, J=9 Hz, 1H), 7.42 (t, J=11 Hz, 1H), 7.76 (d, J=14 Hz, 1H), 8.45 (s, 1H).

EXAMPLE 3

7-(3-amino-3-methylazetidin-1-yl)-1-(3-amino-4,6-difluorophenyl)-6-fluoro-8-methyl-1,4-dihydro-4-oxoguinoline-3-carboxylic Acid The procedure of Example 2 was repeated except that 3-aminoazetidine·dichloride was replaced with 110 mg of 3-amino-3-methylazetidine·dichloride to obtain the title compound.
Characteristic features: pale yellow powder Melting point: 209–222° C. $^1$HNMR (d6-DMSO) δ; 1.37 (s, 3H), 1.63 (s, 3H), 3.83–3.94 (m, 1H), 3.95–4.13 (m, 3H), 5.46 (brs, 2H), 7.04 (t, J=9 Hz, 1H), 7.40 (t, J=11 Hz, 1H), 7.76 (d, J=14 Hz, 1H), 8.48 (s, 1H)

REFERENCE EXAMPLE 5

Preparation of ethyl 1-(4-fluoro-2-methylphenyl)-6,7-difluoro-8-methyl-1,4-dihydro-4-oxoguinoline-3-carboxylate The procedure of Reference Example 3 was repeated except that N-tert-butoxycarbonyl-4,6-difluoro-m- phenylenediamine was replaced with 1.4 g of 4-fluoro-2-methylaniline to obtain the title compound.
Characteristic features: pale yellow powder
Melting point: 187–189° C. $^1$HNMR (CDCl$_3$) δ; 1.40 (t, J=7 Hz, 3H), 1.64 (d, J=3 Hz, 3H), 2.08 (s, 3H), 4.39 (q, J=7 Hz, 2H), 7.06–7.17 (m, 2H), 7.34 (t, J=5 Hz, 1H), 8.22–8.35 (m, 2H).

REFERENCE EXAMPLE 6

Preparation of ethyl 1-(4-fluoro-2-methyl-5-nitrophenyl)-6,7-difluoro-8-methyl-1,4-dihydro-4-oxoguinoline-3-carboxylate To solution of 1.7 g of ethyl 1-(4-fluoro-2-methylphenyl)-6,7-difluoro-8-methyl-1,4-dihydro-4-oxoquinoline-3-carboxylate obtained in the Reference Example 5 in 5 ml of sulfuric acid was incrementally added 480 mg of potassium nitrate on ice. After the addition, the mixture was stirred at room temperature overnight and the reaction solution was poured into ice water and stirred. Chloroform and water were added for separation, and the organic layer was dried over magnesium sulfate and the solvent was distilled off. The solid precipitate was collected by filtration and washed with ethanol to obtain 1.6 g of the title compound.
Characteristic features: pale yellow powder
Melting point: 211–214° C. $^1$HNMR (CDCl$_3$) δ; 1.40 (t, J=7 Hz, 3H), 1.69 (d, J=3 Hz, 3H), 2.20 (s, 3H), 4.40 (q, J=7 Hz, 2H), 7.39 (d, J=11 Hz, 1H), 8.19 (d, J=7 Hz, 1H), 8.23–8.35 (m, 2H)

REFERENCE EXAMPLE 7

Preparation of ethyl 1-(4-fluoro-3-formylamino-6-methylphenyl)-6,7-difluoro-8-methyl-1,4-dihydro-4-oxoguinoline-3-carboxylate 16 m of formic acid was added to 1.6 g of ethyl 1-(4-fluoro-2-methyl-5-nitrophenyl)-6,7-difluoro-8-methyl-1,4-dihydro-4-oxoquinoline-3-carboxylate obtained in the Reference Example 6 and dissolved. 2.1 g of iron powder was added, and the mixture was stirred at 70° C. for 90 minutes. The reaction solution was allowed to cool, and the catalyst was filtered off by celite, and the solvent was distilled off the filtrate. The solid precipitate was collected by filtration and washed with ethanol to obtain 1.6 g of the title compound.
Characteristic features: pale brown powder
Melting point: 246–249° C.

REFERENCE EXAMPLE 8

Preparation of 1-(3-amino-4-fluoro-6-methylphenyl)-6,7-difluoro-8-methyl-1,4-dihydro-4-oxoguinoline-3-carboxylic Acid The procedure of Reference Example 4 was repeated except that ethyl 1-(3-tert-butoxycarbonylamino-4,6-difluorophenyl)-6,7-difluoro-8-methyl-1,4-dihydro-4-oxoquinoline-3-carboxylate was replaced with 1.6 g of ethyl 1-(4-fluoro-3-formylamino-6-methylphenyl)-6,7-difluoro-8-methyl-1,4-dihydro-4-oxoquinoline-3-carboxylate obtained in the Reference Example 7 to obtain the title compound.
Characteristic features: colorless powder
Melting point: 248–250° C. $^1$HNMR (d$_6$-DMSO) δ; 1.76 (d, J=3 Hz, 3H), 1.83 (s, 3H), 6.98 (d, J=8 Hz, 1H), 7.16 (d, J=12 Hz, 1H), 8.27 (t, J=9 Hz, 1H), 8.50 (s, 1H)

EXAMPLE 4

7-(3-aminoazetidin-1-yl)-1-(3-amino-4-fluoro-6-methylphenyl)-6-fluoro-8-methyl-1,4-dihydro-4-oxoguinoline-3-carboxylic Acid The procedure of Example 1 was repeated except that 1-(3-amino-4,6-difluorophenyl)-6,7-difluoro-8-methyl-1,4-dihydro-4-oxoquinoline-3-carboxylic acid was replaced with 110 mg of 1-(3-amino-4-fluoro-6-methylphenyl)-6,7-difluoro-8-methyl-1,4-dihydro-4-oxoquinoline-3-carboxylic acid obtained in the Reference Example 8 to obtain the title compound.
Characteristic features: pale yellow powder
Melting point: 162–169° C. $^1$HNMR (d$_6$-DMSO) δ; 1.55 (s, 3H), 1.79 (s, 3H), 3.67–3.78 (m, 2H), 3.83–3.94 (m, 1H), 4.35–4.50 (m, 2H), 5.41 (brs, 2H), 6.92 (d, J=8 Hz, 1H), 7.09 (d, J=12 Hz, 1H), 7.79 (d, J=14 Hz, 1H), 8.34 (s, 1H).

EXAMPLE 5

7-(3-amino-3-methylazetidin-l-yl)-1-(3-amino-4-fluoro-6-methylphenyl)-6-fluoro-8-methyl-1,4-dihydro-4-oxoguinoline-3-carboxylic Acid The procedure of Example 1 was repeated except that 1-(3-amino-4,6-difluorophenyl)-6,7-difluoro-8-methyl-1,4-dihydro-4-oxoquinoline-3-carboxylic acid was replaced with 180 mg of 1-(3-amino-4-fluoro-6-methylphenyl)-6,7-difluoro-8-methyl-1,4-dihydro-4-oxoquinoline-3-carboxylic acid obtained in the Reference Example 8, and 3-aminoazetidine·dichloride was replaced with 110 mg of 3-amino-3-methylazetidine·dichloride to obtain the title compound.
Characteristic features: pale yellow powder
Melting point: 242–247° C. $^1$HNMR (d$_6$-DMSO) δ; 1.36 (s, 3H), 1.54 (s, 3H), 1.78 (s, 3H), 3.77–3.85 (m, 1H), 3.95–4.09 (m, 3H), 5.44 (brs, 2H), 6.93 (d, J=9 Hz, 1H), 7.09 (d, J=12 Hz, 1H), 7.88 (d, J=14 Hz, 1H), 8.34 (s, 1H).

EXAMPLE 6

1-(3-amino-4-fluoro-6-methylphenyl)-6-fluoro-8-methyl-7-(3-methylaminoazetidin-1-yl)-1,4-dihydro-4-oxoguinoline-3-carboxylic Acid The procedure of Example 1 was repeated except that 1-(3-amino-4,6-difluorophenyl)-6,7-difluoro-8-methyl-1,4-dihydro-4-oxoquinoline-3-carboxylic acid was replaced with 180 mg of 1-(3-amino-4-fluoro-6-methylphenyl)-6,7-difluoro-8-methyl-1,4-dihydro-4-oxoquinoline-3-carboxylic acid obtained in the Reference Example 8, and 3-aminoazetidine·dichloride was replaced with 110 mg of 3-N-methylaminoazetidine·dichloride to obtain the title compound.
Characteristic features: pale yellow powder
Melting point: 235–237° C. $^1$HNMR (d$_6$-DMSO) δ; 1.56 (s, 3H), 1.80 (s, 3H), 2.20 (s, 3H), 3.77–3.90 (m, 1H), 3.90–4.02 (m, 1H), 4.31–4.59 (m, 2H), 5.44 (brs, 2H), 6.91 (d, J=8 Hz, 1H), 7.10 (d, J=11 Hz, 1H), 7.89 (d, J=14 Hz, 1H), 8.34 (s, 1H).

REFERENCE EXAMPLE 9

Preparation of ethyl 1-(2-chloro-4-fluorophenyl)-6,7-difluoro-8-methyl-1,4-dihydro-4-oxoguinoline-3-carboxylate The procedure of Reference Example 3 was repeated except that N-tert-butoxycarbonyl-4,6-difluoro-m-phenylenediamine was replaced with 1.6 g of 2-chloro-4-fluoroaniline to obtain the title compound.
Characteristic features: pale yellow powder
Melting point: 188–191° C. $^1$HNMR (CDCl$_3$) δ; 1.40 (t, J=7 Hz, 3H), 1.77 (d, J=3 Hz, 3H), 4.39 (q, J=7 Hz, 2H), 7.34–7.47 (m, 3H), 8.23 (t, J=10 Hz, 1H), 8.31 (m, 1H).

REFERENCE EXAMPLE 10

Preparation of ethyl 1-(2-chloro-4-fluoro-5-nitrophenyl)-6,7-difluoro-8-methyl-1,4-dihydro-4-oxoguinoline-3-carboxylate The procedure of Reference Example 6 was repeated except that ethyl 1-(4-fluoro-2-methylphenyl)-6,7-difluoro-8-methyl-1,4-dihydro-4-oxoquinoline-3-carboxylate was replaced with 1.8 g of ethyl 1-(2-chloro-4-fluorophenyl)-6,7-difluoro-8-methyl-1,4-dihydro-4-oxoquinoline-3-carboxylate obtained in the Reference Example 9 to obtain the title compound.

Characteristic features: pale yellow powder

Melting point: 253–256° C. $^1$HNMR (CDCl$_3$) δ; 1.40 (t, J=7 Hz, 3H), 1.83 (d, J=2 Hz, 3H), 5 4.39 (q, J=7 Hz, 2H), 7.62 (d, J=9 Hz, 1H), 8.13 (d, J=7 Hz, 1H), 8.23 (t, J=9 Hz, 1H), 8.29 (s, 1H).

REFERENCE EXAMPLE 11

Preparation of ethyl 1-(6-chloro-4-fluoro-3-formylaminophenyl)-6,7-difluoro-8-methyl-1,4-dihydro-4-oxoguinoline-3-carboxylate The procedure of Reference Example 7 was repeated except that ethyl 1-(4-fluoro-2-methyl-5-nitrophenyl)-6,7-difluoro-8-methyl-1,4-dihydro-4-oxoquinoline-3-carboxylate was replaced with 1.6 g of ethyl 1-(2-chloro-4-fluoro-5-nitrophenyl)-6,7-difluoro-8-methyl-1,4-dihydro-4-oxoquinoline-3-carboxylate obtained in the Reference Example 10 to obtain the title compound.

Characteristic features: pale brown powder

Melting point: 261–263° C. $^1$HNMR (d$_6$-DMSO) δ; 1.26 (t, J=7 Hz, 3H), 1.78 (s, 3H), 4.23 (q, J=7 Hz, 2H), 7.94 (d, J=10 Hz, 1H), 8.08 (d, J=9 Hz, 1H), 8.34–8.47 (m, 2H), 8.50 (s, 1H).

REFERENCE EXAMPLE 12

Preparation of 1-(3-amino-6-chloro-4-fluorophenyl)-6,7-difluoro-8-methyl-1,4-dihydro-4-oxoguinoline-3-carboxylic Acid The procedure of Reference Example 4 was repeated except that ethyl 1-(3-tert-butoxycarbonylamino-4,6-difluorophenyl)-6,7-difluoro-8-methyl-1,4-dihydro-4-oxoquinoline-3-carboxylate was replaced with 1.7 g of ethyl 1-(6-chloro-4-fluoro-3-formylaminophenyl)-6,7-difluoro-8-methyl-1,4-dihydro-4-oxoquinoline-3-carboxylate obtained in the Reference Example 11 to obtain the title compound.

Characteristic features: pale yellow powder

Melting point: >258° C. (decomposed) $^1$HNMR (d$_6$-DMSO) δ; 1.18 (d, J=3 Hz, 3H), 5.60–5.91 (br, 2H), 7.10 (d, J=7 Hz, 1H), 7.59 (d, J=10 Hz, 1H), 8.26 (t, J=9 Hz, 1H), 8.71 (s, 1H).

EXAMPLE 7

7-(3-aminoazetidin-1-yl)-1-(3-amino-6-chloro-4-fluorophenyl)-6-fluoro-8-methyl-1,4-dihydro-4-oxoguinoline-3-carboxylic Acid The procedure of Example 1 was repeated except that 1-(3-amino-4,6-difluorophenyl)-6,7-difluoro-8-methyl-1,4-dihydro-4-oxoquinoline-3-carboxylic acid was replaced with 110 mg of 1-(3-amino-6-chloro-4-fluorophenyl)-6,7-difluoro-8-methyl-1,4-dihydro-4-oxoquinoline-3-carboxylic acid obtained in the Reference Example 12 to obtain the title compound.

Characteristic features: pale yellow powder

Melting point: >175° C. (decomposed) $^1$HNMR (d$_6$-DMSO) δ; 1.65 (s, 3H), 3.69–3.81 (m, 2H), 3.84–3.96 (m, 1H), 4.39–4.50 (m, 2H), 5.65 (brs, 2H), 7.05 (d, J=7 Hz, 1H), 7.54 (d, J=10 Hz, 1H), 7.77 (d, J=14 Hz, 1H), 8.50 (s, 1H).

EXAMPLE 8

1-(3-amino-4,6-difluorophenyl)-6-fluoro-7-(3-hydroxyazetidin-1-yl)-8-methyl-4-oxo-1,4-dihydroquinoline-3-carboxylic Acid 70 mg of 3-hydroxyazetidine monochloride, 200 mg of 1,8-diazabicyclo[5.4.0]-7-undecene, and 200 mg of pyridine were stirred at 80° C., and to this mixture was added 150 mg of 1-(3-amino-4,6-difluorophenyl)-6,7-difluoro-8-methyl-4-oxo-1,4-dihydroquinoline-3-carboxylic acid. The mixture was stirred at 90° C. for 10 minutes. Diethylether was added to the reaction solution, and the solution was decanted. 1 ml of ethanol was added to the residue and the solid precipitate was collected by filtration and dried to obtain 70 mg of the title compound.

Characteristic features: pale yellow powder

Melting point: 206–208° C. $^1$HNMR (d$_6$-DMSO) δ; 1.63 (s, 3H), 3.88–3.95 (m, 1H), 3.95–4.02 (m, 1H), 4.44–4.56 (m, 3H), 5.48 (brs, 2H), 5.70 (brs, 1H), 7.02 (t, J=9 Hz, 1H), 7.42 (t, J=11 Hz, 1H), 7.78 (d, J=13 Hz, 1H), 8.49 (s, 1H).

EXAMPLE 9

1-(3-amino-4-fluoro-6-methylphenyl)-6-fluoro-7-(3-hydroxyazetidin-1-yl)-8-methyl-4-oxo-1,4-dihydroquinoline-3-carboxylic Acid 70 mg of 3-hydroxyazetidine monochloride, 200 mg of 1,8-diazabicyclo[5.4.0]-7-undecene, and 200 mg of pyridine were stirred at 80° C., and to this mixture was added 150 mg of 1-(3-amino-4-fluoro-6-methylphenyl)-6,7-difluoro-8-methyl-4-oxo-1,4-dihydroquinoline-3-carboxylic acid. The mixture was stirred at 90° C. for 20 minutes. Diethylether was added to the reaction solution, and the solution was decanted. 1 ml of ethanol was added to the residue and the solid precipitate was collected by filtration and dried to obtain 70 mg of the title compound.

Characteristic features: pale yellow powder

Melting point: 147–151° C. $^1$HNMR (d$_6$-DMSO) δ; 1.55 (s, 3H), 1.82 (s, 3H), 3.85–3.95 (m, 1H), 3.95–4.03 (m, 1H), 4.40–4.53 (m, 3H), 5.43 (brs, 2H), 5.68 (brs, 1H), 6.91 (d, J=8 Hz, 1H), 7.10 (d, J=10 Hz, 1H), 7.81 (d, J=14 Hz, 1H), 8.35 (s, 1H).

REFERENCE EXAMPLE 13

Preparation of 2,4,5-trifluoro-3,6-dimethylbenzoic Acid 70 ml of 1.69M n-hexane solution of n-butyllithium was added dropwise to solution of 18 ml of diisopropylamine in 75 ml of tetrahydrofuran at −65 ° C. under nitrogen stream, and the mixture was stirred at the same temperature for 15 minutes. To the solution was added dropwise solution of 9.5 g of 2,4,5-trifluoro-3-methylbenzoic acid in 75 ml of tetrahydrofuran at −60° C., and the mixture was stirred at the same temperature for 15 minutes. To the solution was added dropwise 9.5 ml of methyl iodide at −70° C., and the mixture was stirred at the same temperature for 30 minutes and overnight at room temperature. Diethylether and water were added for separation, and the aqueous layer was collected.

The aqueous layer was acidified by adding conc. hydrochloric acid, and extracted with diethylether. The organic layer was dried over ahnydrous magnesium sulfate, and the solvent was distilled off under reduced pressure to obtain 6.6 g of the title compound.
Characteristic features: pale yellow powder
Melting point: 118–119° C. $^1$HNMR (CDCl$_3$) δ; 2.23 (s, 3H), 2.40 (s, 3H).

REFERENCE EXAMPLE 14

Preparation of ethyl 2,4,5-trifluoro-3,6-dimethylbenzoyl Acetate

To 400 mg of magnesium were added 1.5 ml of ethanol and 0.05 ml of carbon tetrachloride, and the mixture was stirred at room temperature. To the thus activated solution was added solution of 2.7 ml of ethyl malonate in 5 ml of tetrahydrofuran, and the mixture was stirred at 80° C. for 4 hours. After allowing to cool, the solution was cooled to −40° C. To solution of 3.3 g of the 2,4,5-trifluoro-3,6-dimethylbenzoic acid obtained in the Reference Example 13 in 5 ml of methylene chloride were added 1.5 ml of oxalyl chloride and 3 drops of N,N-dimethylformamide and the mixture was stirred at room temperature for 3 hours. The solvent and the reagent were distilled off under reduced pressure. Toluene was added for azeotropic distillation, and solution of the residue in 5 ml of tetrahydrofuran was added dropwise to the above-described reaction solution at −40° C. After the dropwise addition, the reaction solution was stirred overnight at room temperature, and the solvent was distilled off. To the residue was added 3 ml of 12N hydrochloric acid to adjust pH to about 2, and the solution was extracted with chloroform. The solvent was distilled off and 10 ml of water and 100 mg of p-toluenesulfonic acid were added to the solution. The solution was stirred under heating and reflux condition for 5 hours. After allowing to cool, the solution was extracted with chloroform, and the organic layer was washed with water, dried over anhydrous magnesium sulfate, and concentrated under reduced pressure. The residue was subjected to silica gel column chromatography and 3.2 g of the title compound as a pale brown oil was obtained from the fractions eluted with ethyl acetate:hexane of 1:10.

REFERENCE EXAMPLE 15

Preparation of ethyl 1-(3-tert-butoxycarbonylamino-4,6-difluorophenyl)-6,7-difluoro-5,8-dimethyl-4-oxo-1,4-dihydroquinoline-3-carboxylate To 3.2 g of the ethyl 2,4,5-trifluoro-3,6-dimethylbenzoyl acetate obtained in the Reference Example 14 were added 7.8 g of anhydrous acetic acid and 2.8 g of triethyl orthoformate, and the mixture was heated under reflux for 4 hours. The reaction solution was allowed to cool, and the reagents and the like were distilled off at reduced pressure. Toluene was added for azeotropic distillation. 10 ml of chloroform was added to the residue, and solution of 2.7 g of N-t-butoxycarbonyl-4,6-difluorophenylenediamine in 5 ml of chloroform was added dropwise. The mixture was stirred overnight at room temperature, and the solvent was distilled off. The residue was subjected to silica gel column chromatography and 4.0 g of aminoacrylate compound as a pale yellow solid product was obtained from the fractions eluted with ethyl acetate:hexane of 1:20.

To the solution of all of the thus obtained aminoacrylate compound in 20 ml of N,N-dimethylformamide was added 1.0 g of potassium carbonate, and the mixture was stirred at 70° C. for 3.5 hours. Ethyl acetate and water were added, and the organic layer separated was collected and dried over anhydrous magnesium sulfate. The solvent was distilled off and the residue was subjected to silica gel column chromatography to obtain 3.0 g of the title compound from the fractions eluted with ethyl acetate:hexane of 1:2.
Characteristic features: pale yellow powder
Melting point: 141–142° C. $^1$HNMR (CDCl$_3$) δ; 1.38 (t, J=7 Hz, 3H), 1.51 (s, 9H), 1.76 (d, J=2 Hz, 3H), 2.86 (d, J=3 Hz, 3H), 4.38 (q, J=7 Hz, 2H), 6.80 (brs, 1H), 7.08 (t, J=10 Hz, 1H), 8.17–8.30 (m, 2H)

REFERENCE EXAMPLE 16

Preparation of 1-(3-amino-4,6-difluorophenyl)-6,7-difluoro-5,8-dimethyl-4-oxo-1,4-dihydroquinoline-3-carboxylic Acid To 1.8 g of the ethyl 1-(3-tert-butoxycarbonylamino-4,6-difluorophenyl)-6,7-difluoro-5,8-dimethyl-4-oxo-1,4-dihydroquinoline-3-carboxylate obtained in the Reference Example 15 was added 10 ml of 12N hydrochloric acid, and the mixture was stirred under heating and reflux condition for 4 hours. After allowing to cool, the solid precipitate was collected by filtration, washed with water and ethanol successively, and dried to obtain 1.2 g of the title compound.
Characteristic features: colorless powder
Melting point: >281° C. (decomposed) $^1$HNMR (d$_6$-DMSO) δ; 1.80 (s, 3H), 2.82 (s, 3H), 7.06 (t, J=8 Hz, 1H), 7.46 (t, J=11 Hz, 1H), 8.62 (s, 1H)

EXAMPLE 10

7-(3-aminoazetidin-1-yl)-1-(3-amino-4,6-difluorophenyl)-6-fluoro-5,8-dimethyl-4-oxo-1,4-dihydroquinoline-3-carboxylic Acid To 100 mg of the 1-(3-amino-4,6-difluorophenyl)-6,7-difluoro-5,8-dimethyl-4-oxo-1,4-dihydroquinoline-3-carboxylic acid obtained in the Reference Example 16 were added 300 mg of pyridine, 70 mg of 3-aminoazetidine·dichloride, and 150 mg of 1,8-diazabicyclo[5.4.0]-7-undecene, and the mixture was heated and stirred at 40° C. for 24 hours. After allowing to cool, the solvent and the like were distilled off under reduced pressure. To the residue was added 1 ml of ethanol, and the solution was allowed to stand for 5 days. The solid content was collected by filtration, washed with ethanol and dried to obtain 15 mg of the title compound.
Characteristic features: pale yellow powder
Melting point: >235° C. (decomposed) $^1$HNMR (d$_6$-DMSO) δ; 1.60 (s, 3H), 2.73 (s, 3H), 3.99–4.08 (m, 1H), 4.08–4.18 (m, 1H), 4.23–4.32 (m, 1H), 4.42–4.56 (m, 2H), 5.49 (brs, 2H), 7.02 (t, J=8 Hz, 1H), 7.39 (t, J=11 Hz, 1H), 8.33 (s, 1H), 8.46 (s, 1H).

REFERENCE EXAMPLE 17

Preparation of 2,4,5-trifluoro-3-methyl-6-nitrobenzoic Acid

To 100 ml of conc. sulfuric acid was dissolved 31 g of 2,4,5-trifluoro-3-methylbenzoic acid, and to this solution was incrementally added 19.5 g of potassium nitrate on ice. The solution was stirred at room temperature for 3 days, and another 1.4 g of potassium nitrate was added on ice. After stirring for 6 hours, the solution was poured into ice water, and the solid precipitate was collected by filtration. The precipitate was dissolved in diethylether and washed with water. The organic layer was dried over anhydrous magnesium sulfate, and the solvent was distilled off. The solid precipitate was collected by filtration to obtain 21 g of the title compound.
Characteristic features: pale yellow powder
$^1$HNMR (CDCl$_3$) δ; 2.38 (s, 3H).

REFERENCE EXAMPLE 18

Preparation of ethyl 2,4,5-trifluoro-3-methyl-6-nitrobenzoyl Acetate

To 2.2 g of magnesium were added 8 ml of ethanol and 0.4 ml of carbon tetrachloride, and the mixture was stirred at room temperature. To the thus activated solution was added solution of 14 ml of ethyl malonate in 40 ml of tetrahydrofuran, and the mixture was stirred at 80° C. for 4 hours. After allowing to cool, the solution was cooled to −40° C. To solution of 20 g of the 2,4,5-trifluoro-3-methyl-6-nitrobenzoic acid obtained in the Reference Example 17 in 40 ml of methylene chloride were added 8.4 ml of oxalyl chloride and 3 drops of N,N-dimethylformamide and the mixture was stirred at room temperature for 3 and a half hours. The solvent and the reagent were distilled off under reduced pressure. Toluene was added for azeotropic distillation, and solution of the residue in 15 ml of tetrahydrofuran was added dropwise to the above-described reaction solution at −40° C. After the dropwise addition, the reaction solution was stirred overnight at room temperature, and the solvent was distilled off. To the residue was added 20 ml of 12N hydrochloric acid to adjust pH to about 2, and the solution was extracted with chloroform. The solvent was distilled off and 50 ml of water and 400 mg of p-toluenesulfonic acid were added to the solution. The solution was stirred under heating and reflux condition for 5 hours. After allowing to cool, the solution was extracted with chloroform, and the organic layer was washed with water, dried over anhydrous magnesium sulfate, and concentrated under reduced pressure. The residue was subjected to silica gel column chromatography and 8.0 g of the title compound as a red oil was obtained from the fractions eluted with ethyl acetate:hexane of 1:10.

REFERENCE EXAMPLE 19

Preparation of ethyl 1-(3-tert-butoxycarbonylamino-4,6-difluorophenyl)-6,7-difluoro-8-methyl-5-nitro-4-oxo-1,4-dihydroquinoline-3-carboxylate To 4 g of the ethyl 2,4,5-trifluoro-3-methyl-6-nitrobenzoyl acetate obtained in the Reference Example 18 were added 8.5 g of anhydrous acetic acid and 3.2 g of triethyl orthoformate, and the mixture was heated under reflux for 2 hours. The reaction solution was allowed to cool, and the reagents and the like were distilled off at reduced pressure. Toluene was added for azeotropic distillation. 10 ml of chloroform was added to the residue, and solution of 3.7 g of N-t-butoxycarbonyl-4,6-difluorophenylenediamine in 20 ml chloroform was added dropwise. The mixture was stirred at room temperature for 3 days, and the solvent was distilled off to obtain 4.8 g of aminoacrylate compound as a pale yellow oil.

To the solution of all of the thus obtained aminoacrylate compound in 15 ml of N,N-dimethylformamide was added 1.4 g of potassium carbonate, and the mixture was stirred at 70° C. for 30 minutes. The solution was allowed to cool, and ethyl acetate and water were added to the solution. The organic layer separated was collected and dried over anhydrous magnesium sulfate. The solvent was distilled off and the residue was subjected to silica gel column chromatography to obtain 4.0 g of the title compound from the fractions eluted with ethyl acetate:hexane of 1:2.
Characteristic features: pale yellow powder
Melting point: 188–189° C. $^1$HNMR (CDCl$_3$) δ; 1.36 (t, J=7 Hz, 3H), 1.52 (s, 9H), 1.88 (d, J=3 Hz, 3H), 4.38 (q, J=7 Hz, 2H), 6.94 (brs, 1H), 7.15 (t, J=10 Hz, 1H), 8.29–8.44 (m, 2H).

REFERENCE EXAMPLE 20

Preparation of ethyl 5-amino-1-(3-amino-4,6-difluorophenyl)-6,7-difluoro-8-methyl-4-oxo-1,4-dihydroquinoline-3-carboxylate To solution of 1.0 g of the ethyl 1-(3-tert-butoxycarbonylamino-4,6-difluorophenyl)-6,7-difluoro-8-methyl-5-nitro-4-oxo-1,4-dihydroquinoline-3-carboxylate obtained in the Reference Example 19 in 5 ml of acetic acid was added 900 mg of iron powder, and the mixture was heated and stirred at 90° C. for 4 hours and 40 minutes. The catalyst in the reaction solution was filtered off by using celite, and the solvent in the residue was distilled off. The residue was subjected to silica gel column chromatography, and ethanol was added to the oil obtained from the fractions eluted with ethyl acetate:hexane of 1:1. The powder precipitate was collected by filtration to obtain 200 mg of the title compound.
Characteristic features: pale yellow powder
Melting point: 134–135° C. $^1$HNMR (d$_6$-DMSO) δ; 1.24 (t, J=7 Hz, 3H), 1.57 (d, J=2 Hz, 3H), 4.19 (q, J=7 Hz, 2H), 5.45 (brs, 2H), 6.95 (t, J=8 Hz, 1H), 7.39 (t, J=11 Hz, 1H), 8.20 (s, 1H).

REFERENCE EXAMPLE 21

Preparation of 5-amino-1-(3-amino-4,6-difluorophenyl-2-yl)-6,7-difluoro-8-methyl-4-oxo-1,4-dihydroquinoline-3-carboxylic Acid To 200 mg of ethyl 5-amino-1-(3-amino-4,6-difluorophenyl)-6,7-difluoro-8-methyl-4-oxo-1,4-dihydroquinoline-3-carboxylate obtained in the Reference Example 20 was added 5 ml of 12N hydrochloric acid, and the mixture was heated under reflux for 10 hours. The reaction solution was allowed to cool, and the solid precipitate was collected by filtration. The precipitate was washed with ethanol, and then with diethylether to obtain 140 mg of the title compound.
Characteristic features: yellow powder
Melting point: >290° C. $^1$HNMR (d$_6$-DMSO) δ; 1.61 (d, J=2 Hz, 3H), 7.02 (t, J=8 Hz, 1H), 7.42 (t, J=11 Hz, 1H), 8.47 (s, 1H).

TEST 1

Antibacterial Activity

Minimum growth inhibitory concentration (MIC, μg/ml) was evaluated in accordance with the standard method of Japan Chemotherapy Society (Chemotherapy 29(1), 76, 1981). The results are shown in Table 1. It should be noted that tosufloxacin was also evaluated for its minimum growth inhibitory concentration for the purpose of comparison. The results are also shown in Table 1.

TABLE 1

|  | S. aureus 209P | P. aeruginosa IFO3445 |
|---|---|---|
| Compound of Ex. 1 | 0.006 | 0.05 |
| Compound of Ex. 2 | 0.006 | 0.1 |
| Compound of Ex. 3 | 0.006 | 0.1 |
| Compound of Ex. 4 | 0.003 | 0.1 |
| Compound of Ex. 5 | 0.013 | 0.2 |
| Compound of Ex. 6 | 0.013 | 0.2 |
| Compound of Ex. 7 | 0.013 | 0.1 |
| Compound of Ex. 8 | 0.006 | 0.2 |
| Compound of Ex. 9 | 0.013 | 0.2 |
| Compound of Ex. 10 | 0.003 | 0.1 |
| Tosufloxacin | 0.05 | 0.39 |

TEST 2

Phototoxicity Test

Female ICR mice (5 to 6 week old) were intravenously administered with the test compound (40 mg/kg/10 ml), and irradiated with UVA (320 to 400 nm, 1.8 mW/cm$^2$/sec) for 4 hours. Abnormality in the ears was monitored at 0 hour immediately after the irradiation and after 24 hours. The ear abnormality was evaluated by the following criteria: no abnormality (0 point), very slight erythema (1 point), well defined erythema (2 points), moderate to severe erythema or edema formation (3 points). The results are shown in Table 2. Tosufloxacin which is a conventional known antibacterial agent was also tested in a similar way for the purpose of comparison. The results are also shown in Table 2.

TABLE 2

|  | 0 hour (point, occurrence) | 24 hours (point, occurrence) |
|---|---|---|
| Compound of Ex. 1 | 0, 0/3 | 0, 0/3 |
| Compound of Ex. 2 | 0, 0/3 | 0, 0/3 |
| Compound of Ex. 3 | 0, 0/3 | 0, 0/3 |
| Compound of Ex. 4 | 0, 0/3 | 0, 0/3 |
| Compound of Ex. 5 | 0, 0/3 | 0, 0/3 |
| Compound of Ex. 6 | 0, 0/3 | 0, 0/3 |
| Compound of Ex. 7 | 0, 0/3 | 0, 0/3 |
| Compound of Ex. 8 | 0, 0/3 | 0, 0/3 |
| Compound of Ex. 9 | 0, 0/3 | 0, 0/3 |
| Compound of Ex. 10 | 0, 0/3 | 0, 0/3 |
| Tosufloxacin | 1.8, 4/5 | 0.8, 4/5 |

TEST 3

Absorption and Excretion

A compound of the present invention was measured for its urine and bile recovery rates in rats after its oral administration to evaluate absorption and excretion of the compounds.

(1) Urine Recovery Rate

Male SD rats of 6 week old which had been fasted overnight were administered orally with 0.5% methylcellulose suspension of the test compounds (20 mg/10 ml/kg). The urine collection was continued until 24 hours after the administration. The concentration of the test compound in the urine was measured by paper disc method using Bacillus subtilis ATCC6633 for the test bacterium to determine the urine recovery rate.

(2) Bile Recovery Rate

Into choledoch duct of male SD rats of 6 week old which had been fasted overnight was inserted a polyethylene tube under etherization. After arousing, the rats were forcedly administered orally with the test compounds as in the case of the above (1), and bile collection was continued until 24 hours after the administration. The bile with no further treatment and the bile alkaline hydrolyzed (with 0.1N NaOH, 37° C., 1 hour) were measured for their concentration of the test compound by the same procedure as in the case of the above (1) to determine the bile recovery rate.

The results are shown in Table 3.

TABLE 3

|  | Recovery rate (24 hours, %) | | | |
|---|---|---|---|---|
|  | Urine | Bile | Bile* | Total recovery rate |
| Compound of Ex. 3 | 3.9 | 10.4 | 26.7 | 30.6 |

*Recovery rate for the bile after alkaline hydrolysis

What is claimed is:

1. A pyridonecarboxylic acid derivative represented by the following formula (1):

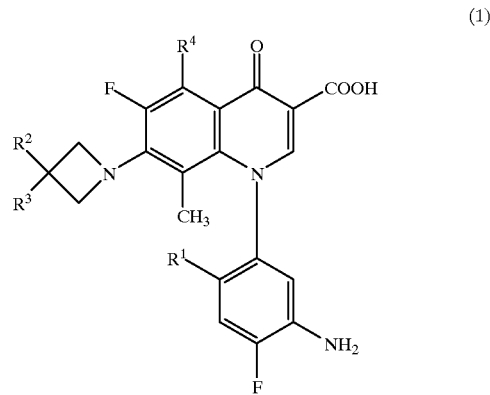

(1)

(wherein $R^1$ represents hydrogen atom, a halogen atom or a lower alkyl group; $R^2$ represents hydrogen atom or a lower alkyl group; $R^3$ represents substituted or unsubstituted amino group or hydroxyl group wherein the substituents of the substituted amino group are selected from the group consisting of a lower alkyl group, a lower alkenyl group, an aralkyl group containing 7 to 11 carbon atoms, an aryl group containing 6 to 14 carbon atoms, a lower alkanoyl group, a lower alkoxycarbonyl group, an aroyl group containing 7 to 15 carbon atoms, and $R^4$ represents hydrogen atom, a lower alkyl group, amino group or nitro group) or its salt.

2. An antibacterial composition comprising:

an effective amount of the pyridonecarboxylic acid derivative or the salt thereof of claim 1 as its effective component; and a carrier therefor.

3. A pyridonecarboxylic acid derivative represented by the following formula (1):

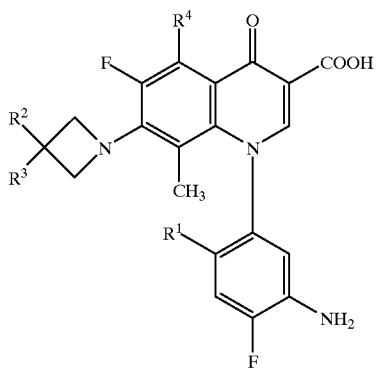
(1)

(wherein $R^1$ represents hydrogen atom, a halogen atom or a lower alkyl group; $R^2$ represents hydrogen atom or a lower alkyl group; $R^3$ represents substituted or unsubstituted amino group or hydroxyl group wherein the substituents of the substituted amino group are selected from the group consisting of methyl, ethyl, n-propyl, i-propyl, n-butyl, i-butyl, t-butyl, pentyl, hexyl, heptyl, vinyl, allyl, 1-propenyl, butenyl, pentenyl, hexenyl, heptenyl, benzyl, 1-phenylethyl, phenyl, naphthyl, formyl, acetyl, propionyl, butyryl, isobutyryl, methoxycarbonyl, ethoxycarbonyl, benzoyl, naphthoyl, and $R^4$ represents hydrogen atom, a lower alkyl group, amino group or nitro group) or its salt.

4. The pyridonecarboxylic acid derivative of claim 1, wherein $R^3$ is said substituted or unsubstituted amino group and $R^4$ is hydrogen.

5. The pyridonecarboxylic acid derivative of claim 3, wherein $R^3$ is said substituted or unsubstituted amino group and $R^4$ is hydrogen.

* * * * *